United States Patent [19]

Wittwer

[11] Patent Number: 4,478,658
[45] Date of Patent: Oct. 23, 1984

[54] METHOD FOR SEALING NON-ENTERIC CAPSULES

[75] Inventor: Fritz Wittwer, Lupsingen, Switzerland

[73] Assignee: Warner-Lambert Company, Morris Plains, N.J.

[21] Appl. No.: 451,573

[22] Filed: Dec. 20, 1982

[51] Int. Cl.³ ............................................. B29C 27/10
[52] U.S. Cl. ....................................... 156/69; 53/399;
53/471; 156/246; 156/277; 156/294; 156/336;
206/530; 206/534; 427/3
[58] Field of Search ..................... 53/471, 399; 156/69,
156/213, 277, 294, 246, 336; 206/528, 530, 532,
534; 426/138; 427/3

[56] References Cited

U.S. PATENT DOCUMENTS

| | | | |
|---|---|---|---|
| 1,861,047 | 5/1932 | Colton | 206/528 X |
| 3,444,290 | 5/1969 | Wai | 206/528 X |
| 3,702,653 | 11/1972 | Mottin et al. | 206/530 X |
| 3,823,816 | 7/1974 | Controulis et al. | 426/138 X |
| 4,322,449 | 3/1982 | Voss et al. | 427/3 |

Primary Examiner—Robert Dawson
Attorney, Agent, or Firm—Louis S. Gillow

[57] ABSTRACT

A method is disclosed for sealing edible capsules comprised of telescopically engaged tubular capsule halves that define a junction seam between them. The method comprises adhesively applying against at least a portion of the seam a frangible, edible label adapted to cover the seam at the point of intersection therewith, and to fracture upon slight displacement of the capsule halves with respect to each other. In one embodiment, the present method comprises the preparation of individual labels, the application to such labels of a quantity of adhesive and the subsequent application of the labels to the capsule. In an alternate embodiment, the labels, comprising a film forming material, are directly applied to the capsule by the projection of a hot melt of the film forming material onto the capsule at the location of the seam. The method may be practiced by means of automated label applying machinery, in the instance of the prior preparation of the labels, and by jet printing techniques in the instance of direct label application. The labels may also be imprinted with suitable indicia, either before or after application to the capsule. The capsules sealed and labeled in accordance with the present method exhibit improved tamper evidence and resistance, as the labels are incapable of cosmetic reconstruction after tampering. In the instance where the label comprises a longitudinal strip extending annularly about the entire capsule seam, the resulting capsule is advantageously rendered fluid-tight.

30 Claims, 7 Drawing Figures

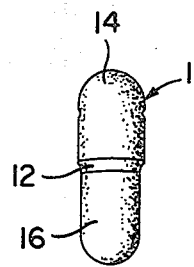
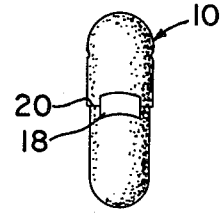
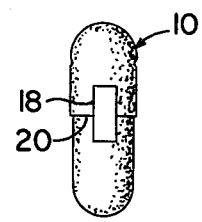
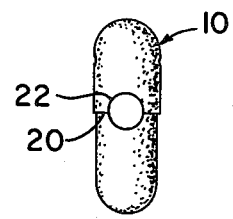
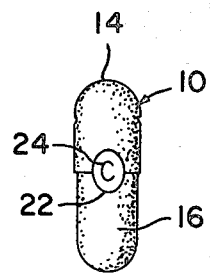
FIG. 1  FIG. 2  FIG. 3  FIG. 4  FIG. 5
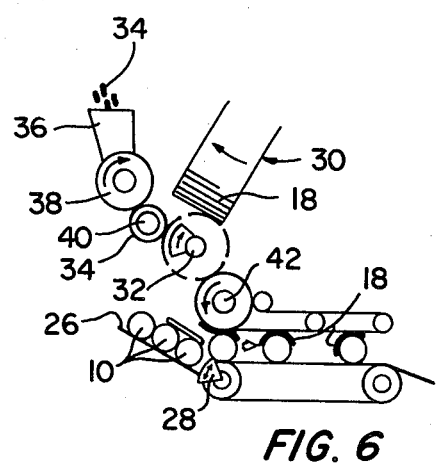
FIG. 6
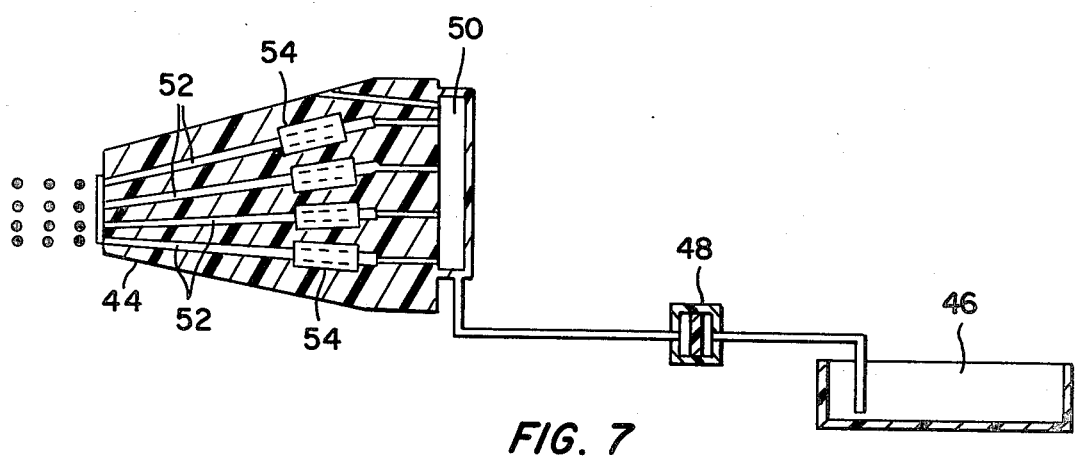
FIG. 7

METHOD FOR SEALING NON-ENTERIC CAPSULES

BACKGROUND OF THE INVENTION

1. Field of the Invention

This invention relates to the preparation of capsules containing edible ingredients, that usually comprise telescopically engaged capsules halves, and more particularly to a method for sealing such capsules to render them tamper-proof and tamper-evident.

2. Description of the Prior Art

The capsules to which the present method relates are well known and have been in broad use for many years. Such capsules are generally prepared from an edible natural substance such as gelatin, and are telescopically engageable tubes, each tube having one end thereof sealed, so that upon co-axial disposition, they are capable of holding a quantity of material. Generally, such capsules are utilized in the pharmaceutical and food industries, to hold edible and pharmaceutically active materials such as medicines, vitamin preparations, and other edibles both solid and liquid. Generally, the materials from which the capsules are prepared are hydrophilic, and thereby adapted to dissolve in the intestine after ingestion.

One of the difficulties that has long been encountered in the use of such capsules as stated, has been their ability and occasional tendency to disengage from each other, whereby the contents of the capsule escape and are lost. Accordingly, the prior art is replete with numerous approaches directed to the maintenance of the sealing engagement between the capsule halves.

The problem of the disengagement of the capsule halves from each other has recently become more acute, in view of the well publicized deliberate disassembly of certain encapsuled medicaments and the inclusion therein of certain poisons such as cyanide. This deliberate act was successfully accomplished because the capsules were inadequately sealed and gave no evidence of their tampering. That is, the slip fit engagement between the capsule halves is easily disrupted and the cap part of the capsule removed, so that an intruder may insert a small but lethal quantity of poison or other disruptive agent therein.

The events described above have spurred a renewed interest on the part of the industry and the public at large to develop methods and associated apparatus to render these capsules tamper-proof by the placement of appropriate indicators of tampering on the capsule. One such approach to this problem is disclosed in U.S. Pat. No. 1,861,047, wherein a circular band of hardened gelatin is disposed about the seam that occurs between the respective capsule halves, comprising the body and the cap part that receives it. The application of the hardened gelatin band is presumed to indicate when the capsule parts have been separated and to thereby offer an indication that tampering has occurred.

The procedure outlined in the '047 patent and the capsules treated thereby have been found to be deficient, in that it is possible to separate the body part from the cap part, modify the contents thereof and thereafter replace the cap and body parts in position against each other and reband the rejoined capsule so as to avoid detection of tampering.

Further, while it is desirable to render the capsules tamper-proof, i.e. resistant or better yet, incapable of disassembly, it is equally desirable to render such capsules tamper-evident, i.e. capable of disassembly, adulteration and reassembly, however, offering visual indication of the same. The need for a tamper-evident seal is far greater, as it is extremely difficult to assure that each capsule will be properly sealed so as to be tamper proof.

SUMMARY OF THE INVENTION

In accordance with the present invention a method for sealing capsules comprising telescopically joined tubular capsule halves having a junction seam, is disclosed which renders such capsules tamper-proof and tamper-evident. The method comprises adhesively applying against at least a portion of the seam, a frangible edible label material adapted to cover that portion of the seam and to fracture upon any displacement of the capsule halves with respect to each other. Thus, even the slightest mechanical force will cause the seal to fracture along a line coincident with the seam, and the resulting fracture will be incapable of repair and obscurity.

In one embodiment of the present method, the label material is prepared as a film, and coated on one surface thereof with an edible adhesive, after which it is applied across the seam of the capsule with the adhesive-coated surface thereagainst. The films may be prepared by well known techniques, such as extruding, casting and the like, and the adhesives may be applied to the film by various techniques as well. Thus, adhesives may be applied by roller coating, brushing, spraying and the like.

In one embodiment of the present invention, the adhesive is applied as a hot melt in liquid form and is sprayed or otherwise appropriately dispensed on the surface of the label.

The advantage of the sealing method of the present invention, is that the labels so applied are incapable of separation from the contiguous outer surfaces of the capsule halves. Thus, one wishing to tamper with a capsule so sealed, must inevitably break the seal along the seam with the consequence that the seal will be incapable of reconstitution, and will offer visual evidence of such tampering.

The labels may be prepared from a number of pharmaceutically acceptable, edible film forming materials, such as natural proteins, cellulose, cellulose derivatives, carbohydrates, vinyl polymers, acrylic polymers, natural gums and mixtures of these. The film forming materials may be prepared in solutions, with edible solvents such as water, lower alkanols, glycols, glycol ethers, ketones, carboxylic acids and the like. Also, other additives may include softeners, colorants, lubricants, antioxidants, and others.

Similarly, the adhesives may be selected from a variety of pharmaceutically acceptable materials such as water, aqueous buffered solutions, preferably in the acidic range, aqueous solutions of lower alkanols, aqueous solutions of natural proteins, aqueous solutions of cellulose derivatives, carbohydrates, natural gums, synthetic polymers, cross linking monomeric materials, and pressure sensitive adhesives prepared from natural and synthetic resins, and mixtures thereof.

The present method may be practiced in a continuous fashion, wherein individual label materials are cast, dried, coated with adhesive and thereafter applied to the assembled capsules. Alternately, the labels may be cast as continuous sheets which are then punched or otherwise cut to form individual labels for later use.

Finally, the labels may bear certain visible indicia, markings, etc., which may be applied either to the labels prior to their application to the capsule, or after the same.

In a preferred embodiment, the present method is practiced with the use of a hot melt adhesive applied first to the label, with the so coated label thereafter applied to the capsule. Also, label shapes may vary from strips adapted to reside annularly in alignment with the seam, or transverse thereto, as well as circular dots or the like that are placed along a portion of the seam. In a preferred embodiment, the label comprises a round patch or dot that is placed in overlapping relationship to the seam.

The adhesive useful in accordance with the present invention may vary. Thus, in one embodiment, the adhesive may be water or steam, the latter in the instance where it is desired to activate the surface of the label to render it tacky and thereby receptive to the capsule surface. The adhesive may also comprise an aqueous solution of materials such as acidic buffer solutions, lower alkanols, proteins, carbohydrates and the like. Yet further, the adhesive may comprise a synthetic cross-linking monomer such as a substituted cyanoacrylate. The adhesive may preferably be pressure sensitive, and includes derivatives of wood rosin, natural and synthetic rubbers, and the like.

In an alternate embodiment of the present invention, the label may be directly applied to the capsule as a hot melt or liquid, without the need for an intermediate formation step followed by adhesive application. In this embodiment, the label may be dispensed by a spraying or preferably, a jet printing technique as is disclosed in my co-pending application Serial No. 444,007, the disclosure of which is incorporated herein by reference.

The present invention may be practiced on a variety of apparatus, including conventional label application machinery. The labels thus applied remain permanently bound to the capsule surfaces, so that even slight dislocation of the capsule halves with respect to each other will cause a fracture to form in the label, and to remain permanently evident and incapable of reconstitution.

Capsules sealed in accordance with the present method exhibit tamper-evident capability as well as substantial improvement in tamper resistance. In the instance where the label is prepared from a material that is applied directly to the capsule seal as a hot melt, the nature of this material is such that attempts to reheat the same after dislocation of the capsule halves with respect to each other, are uniformly unsuccessful. In most instances, the capsule walls appear to lose their crystallinity and corresponding strength as a result of apparent exposure to the temperatures at which the hot melt is applied, so that attempts to dislodge the cap part from the body part of the capsule frequently result in total disintegration thereof.

The present method may be practiced continuously in all of its variant forms, and is therefore susceptible of high speed, commercial application. As the label may comprise a rounded patch or dot, such as a circle, and may thereby be applied by a direct technique such as jet printing of a hot melt, the expense and disruption of encapsulated product manufacture and packaging is minimized. The resulting capsules, however, offer greater security and promote improved user confidence.

Accordingly, it is a principal object of the present invention to provide a method for sealing telescopically engageable capsule members to render them tamper-evident.

It is a further object of the present invention to provide a method as aforesaid that results in the formation of a seal at the seam defining each of the capsule halves, that serves as a deterrent to disassembly of the capsule.

It is a further object of the present invention to provide a method as aforesaid that is simply and expensively practiced, and yields uniformly reliable results.

It is a still further object of the present invention to provide a method as aforesaid that yields a capsule seal incapable of cosmetic reconstruction after fracture.

Other objects and advantages will become apparent to those skilled in the art from a review of the ensuing description that proceeds with reference to the following illustrative drawings.

BRIEF DESCRIPTION OF THE DRAWINGS

FIGS. 1-4 are front perspective views illustrating typical capsules sealed in accordance with the present invention.

FIG. 5 is a perspective view of the capsule of FIGURE 4, illustrating the application of printed indicia to the label.

FIG. 6 is a schematic illustration of a label applying apparatus useful in the present invention. FIG. 7 is a side sectional view illustrating a jet printing apparatus useful in an alternate embodiment of the present invention.

DETAILED DESCRIPTION

In accordance with the present invention, a method for sealing edible capsules is disclosed which renders the capsules tamper-proof and tamper-evident. The method comprises adhesively applying to the capsule against at least a portion of the seam defined by the respective capsule halves, a frangible edible label adapted to cover the seam at the point of its intersection with the same, and to fracture upon displacement of the capsule halves with respect to each other. The present method may comprise preparing a label, applying an adhesive to one side of the label and thereafter applying the label with its adhesive coated surface against the capsule seam.

Alternately, the label may be prepared and directly applied to the capsule, as in the instance where the label material is a heated liquid that is directed against the capsule's outer wall. In such instance, it may be unnecessary to utilize the intermediate adhesive, as the label material will possess sufficient adhesive properties to form a durable bond with the outer wall of the capsule. Both this technique and the embodiment discussed earlier will be developed later on herein.

The labels may be prepared from a variety of edible film forming materials that are pharmaceutically acceptable. In most instances, these materials are hydrophilic, in that they are water soluble and therefore dissolve readily in the intestinal fluids. Suitable film forming materials may be selected from the group consisting of natural proteins, cellulose and its derivatives, carbohydrates, vinyl polymers, acrylic polymers, natural gums and mixtures of these. More particularly, the film forming material may be selected from the group consisting of gelatin, collagen, cellulose, cellulose ethers and esters, modified and unmodified starches, substituted and unsubstituted polyvinyl acetate, polymers and co-polymers of acrylic acid and methacrylic acid, and their salts and esters, natural gums such as gum arabic, gum tragacanth, locust bean gum, guar gum, and mixtures of the above.

Cellulosic materials would include lower alkyl substituted cellulose such as methyl cellulose and ethyl cellulose, as well as salts such as sodium carboxymethyl cellulose. Starches would include potato starch, wheat starch, maize starch, corn starch, rice starch and the like; pregelatinized starches, dextrins, starch acetates, starch phosphates, and other modified starches.

In the instance where the label is to be preliminarily formed and thereafter applied to the capsule, the film forming material may be combined with a suitable solvent to faciliate the preparations of solutions, dispersions or emulsions of the aforementioned polymer materials. Suitable solvents include water; lower alkyl alcohols having 1-8 carbon atoms; glycols, and in particular, lower alkyl glycols and ethers thereof; lower alkyl ketones having 1-8 carbon atoms; lower alkyl esters of alkyl carboxylic acids, wherein lower alkyl is defined as ranging from 1-8 carbon atoms; and mixtures of the same. The solvents may be present in a variety of concentrations, depending upon the viscosity that is desired. For example, a suitable range of solvent is between 1% and 70% by weight of the polymer.

In addition, the solutions, dispersions, etc. of the film forming polymers or materials may include other additives such as softeners. Suitable softeners include polyols such as glycerol, sorbitol, mannitol and the like; polyglycols such as polyethylene glycol and polypropylene glycol; dialkylphthalates, wherein a lower alkyl such a butyl is utilized; lower alkyl citrates having 1 to 6 carbon atoms, esters of polyols such as the mono-,di-, and tri-acetates of glycerol; and long chain fatty acids such as ricineoleic acid and esters thereof. The softeners are generally present in an amount ranging from about 0.1 to about 50% by weight based on the polymer solids.

Similarly, colorants may be added, particularly as they render the label more difficult to duplicate in the event of fracture from tampering. Suitable colorants include those that are pharmaceutically acceptable, such as the synthetic dyes defined as Food, Drug and Cosmetic Grade, inorganic oxides such as iron oxide, titanium dioxide, and other known materials. The colorants may be used at concentrations ranging from about 0.001 to about 10%, and preferably between 0.010 and 5% based upon the weight of the film forming polymer.

Additionally, ingredients such as lubricants may be added in small quantities, for example, less than 10% by weight of the polymer solids. Suitable lubricants include talc, magnesium stearate and the like.

The foregoing materials may be combined and suitable films prepared which may be thereafter cut or punched to form the desired label shape. The preparation of the films may vary in accordance with the art, and may be accomplished by continuous roller or knife coating, spraying, casting on horizontal flat surfaces and the like. In each instance, the films may be peeled from the forming surface or substrate and thereafter punched or otherwise cut to form the desired label shapes.

An optional post treatment of the label films may be useful, in the instance where, for example, the labels prepared from a gelatin dispersion. In such instance, a pharmaceutically acceptable cross-linking agent such as formaldehyde, glutaraldehyde, carbodiimides and the like may be prepared in aqueous solutions and sprayed or otherwise applied to the surface of relatively freshly formed gelatin films. This treatment, when compatible with the end use of the capsule to be sealed, has the effect of embrittling the gelating label to enhance frangibility and corresponding tamper-evident capability.

In the first embodiment of the present method, wherein labels are individually prepared before application to the capsules, the film forming material described above may be appropriately prepared and films developed with thicknesses ranging, for example, between 10 and 500 microns, and preferably, between and 60 microns. As mentioned earlier, the labels may be punched, cut, etc., to a variety of suitable shapes, among them rectangular, circular or oval. Referring now to FIGS. 1-4, capsules having labels of various shapes disposed thereon, are illustrated. In FIG. 1, capsule 10 is illustrated with a label 12 that is shown extending annularly about the entire capsule, so as to cover the seam, not visible herein. In this embodiment, the total encirclement of the capsule 10 by the label 12 offers the added effect of tightening the cap part 14 about the body part 16, to enhance the fluid-retaining capability of the capsule. Such capsules would therefore be well suited for containing liquids, pastes or the like.

A variant label is shown in FIG. 2, wherein a finite rectangular strip 18 is placed along the seam 20 of capsule 10. For example, in the instance where a conventionally sized capsule is concerned, rectangular strip 18 may, for example, have a length ranging from about 5 to about 31 mm and a width ranging from about 3 to about 7 mm. Naturally, these exact dimensions are illustrative only and will vary depending upon discretion and capsule size.

In an alternate application, strip 18 may be applied with its longitudinal dimension transverse to the direction of seam 20, as shown in FIG. 3. A preferred label is shown in FIG. 4, wherein a rounded or circular patch 22 is shown. Exemplary dimensions of patch 22 in the instance of a circular perimeter, comprise a diameter ranging from 3 to 10 mm. Such dimensions are offered as illustrative only.

In the instance where a label is prepared and thereafter applied to the capsule wall, an adhesive composition is preferably applied to one surface of the label. Suitable adhesives are likewise selected from pharmaceutically acceptable materials, and may comprise water and steam; aqueous acidic buffer solutions; aqueous solutions of lower alcohols; aqueous solutions of natural proteins dissolved in alkaline solutions; aqueous solutions or dispersions of starches; cellulose derivatives; carbohydrates including gums, sugars and the like; and synthetic polymers such as polyvinyl alcohol, polyvinylpyrrolidone, and similar materials.

The adhesives may also include organic solutions of nitrocellulose, polyvinylacetate and the like, in organic solvents with low boiling points, such as methyl or ethyl acetate, methanol, methylene chloride, and mixtures of these. The adhesives known as "instant glues" are also contemplated, and would include pure monomeric methyl or ethylcyanoacrylates.

In addition to the adhesive materials mentioned above, others materials identified as "hot-melt" materials are contemplated herein, which would be applied by appropriate techniques against the surface of the label. Thus, such "hot-melt" materials would include hydropolymers such as gelatin, dextrins and the like; natural and synthetic polymers, such as cellulose derivatives, vinyl polymers, including esters and acetals. These materials would, for example, contain on the order of 20% of water, and would be kept molten at temperatures ranging from about 80° to 130° C., at which temperatures they would be applied to the label surface.

In a particular embodiment of the invention, the adhesive composition may be pressure-sensitive. This type of adhesive has particular advantages, in that it simplifies the application of the label to the capsule wall, eliminating the need for the application of either heat or solvents to render the adhesive surface active. Suitable pressure sensitive adhesive compositions include those based on wood rosin, natural or synthetic terpene resins, coumarone-indene resins, natural rubbers, synthetic rubbers such as butadiene-styrene, isobutylene-isoprene copolymers, polyisobutylene, polyacrylic acids and esters thereof, and copolymers of these materials. As with the other adhesive compositions, the pressure-sensitive adhesives may be applied by any one of numerous well known techniques, such as dipping, spraying, roller coating and the like. Additional adhesives may be utilized in accordance with the teachings of my copending application Serial No 451,500, filed concurrently herewith, the disclosure of which is incorporated herein by reference.

The adhesive compositions may include other additives such as softeners, antioxidants and other of the materials recited with respect to the film forming compositions. Naturally, all of these materials must be pharmaceutically acceptable to find use herein.

The adhesive may be applied to the surface of the label in amounts which vary depending upon the nature of the adhesive and the dimensions of the labels themselves. For example, the adhesive may be applied in amounts ranging from about 2 to about 10 microliters per label, in the instance where the labels conform in size to the approximate dimensions set forth earlier herein.

The temperature at which the adhesives may be applied may vary with the specific adhesive. For example, the cyanoacrylate adhesives are utilized at room temperature, while the hot-melt adhesives are preferably utilized at temperatures ranging between 70 and 100° C.

With respect to the hot-melt adhesives, an advantage of these materials, mentioned earlier, is that they offer an increased margin of safety against tampering, by their effect upon the capsule wall. That is, the temperature of these adhesives causes a local remelting of the capsule wall which enhances the adhesive bond between the label and the wall, and also tends to embrittle the wall due to the rapid cooling thereof that takes place after the adhesive is applied. The combined effect of these events enhances the frangibility of the capsule wall and this altered property, in combination with the improved adhesion of the label increases the likelihood of disintegration of the capsule in response to a tampering attempt.

The first aspect of the present method, discussed above, relates to the sequential preparation of the label, followed by the application of an adhesive to a surface of the label, and the subsequent application of the label to the capsule. While this procedure may be performed manually, it is to be understood that automated operation of this method is commercially necessary and desirable. Referring now to FIG. 6, a schematic diagram of a known label applying machine is shown, which may be utilized in accordance with the present invention. The machine illustrated in FIG. 6 is commercially available.

Briefly, the operation of the machine proceeds as follows. The capsules 10 enter the machine via an infeed shute or incline 26 and are sequentially urged into position for application of labels 18 by a pusher device 28. Labels 18 are extracted from an oscillating magazine 30 by label carrier 32 having on its surface a coating of adhesive 34. A quantity of adhesive 34 is contained within feed hopper 36 and is uniformly dispensed upon roller 38 which in turn transfers the adhesive layer to intermediate roller 40, that applies the coating to label carrier 32. Thus, label carrier 32 extracts a label 18 and rotates to transfer it to the labeling cylinder 42 which in turn makes contact with the capsule 10 as shown.

After the label 18 is applied to the surface of capsule 10, the capsules are non-rotatably transported out of the machine, for packaging or storage.

The machine just described is representative of a variety of automated apparatus useful for the sequential application of labels to capsules.

Numerous alternate apparatus may be used to practice the foregoing method, and representative alternates of them are discussed though not illustrated. For example, the adhesive may be applied by suitable spray guns directed at labels transferred along a vacuum conveyor or roll, and thereafter either heated to dry the adhesive or directly index into contact with the capsule. In a modification of this concept, a vacuum cylinder bearing a regularly spaced plurality of labels may first make contact with a roller coater or other coating device for the dispensing of a quantity of adhesive, after which the vacuum conveyor or cylinder may index into position either for the drying of the adhesive or for the direct application of the adhesive-coated label to a capsule. All of the foregoing techniques, including the application of the adhesive to labels as a hot-melt, may be performed with equipment known in the art, and further discussion thereof is not believed necessary herein.

Further, self adhesive labels as known in the art may be prepared and used herein. For example, a plurality of such labels may be disposed along a carrier web and would be capable of indexing into position adjacent consecutive capsules for autogenous transfer to the capsule walls. Such self adhesive label would include labels bearing pressure-sensitive adhesives, as well as labels having one of their surfaces sensitized to exhibit and adhesive affinity for the capsule walls.

In an alternate embodiment of the present invention, the label material may be applied directly to the capsule as a hot-melt, or as an emulsion, solution or the like, by jet printing techniques. Referring now to FIG. 7, a representative multi nozzle jet printing nozzle assembly is illustrated, which is the subject of European Patent Publication No. 011 269 A1, by Gunther M. Voss and Peter Gruber. The disclosure of this patent is incorporated herein by reference.

Briefly with reference to FIG. 7, the multi channeled nozzle assembly 44 draws the printable fluid from a fluid tank 46, through a conduit with a filter 48 and thence to a fluid distribution chamber 50 where it is introduced into a plurality of nozzle elements 52, each of which has at its proximal end a piezoelectric transducer 54. Each transducer 54 serves the function of causing the relatively high viscosity incoming fluid to oscillate and thereby to break into droplets such as those illustrated at 56, which may then effectively and rapidly exit the nozzle elements 52. This technology is well known with respect to contactless printing, and is also the subject of my co-pending application Serial No.

44,007 directed to an apparatus and method for sealing capsules, the entire disclosure of which has been incorporated herein by reference.

Thus, by the representative apparatus described in FIG. 7, a quantity of the film forming materials suitable for label preparation may be maintained in liquid form and appropriately dispensed with great accuracy against the seam of a capsule, to form the desired label. This particular technique is useful in the instance where excessive handling of the capsule is undesirable, as contactless application avoids the problems associated with the forces exerted upon the capsule during label application. Naturally, contactless printing of this type is illustrative of but one technique for the direct application of label material to the capsule, and the invention should not be construed as limited to this illustrated technique.

In addition to the application of the label to the capsule, imprinting of logos, codes or the like may be placed on the visible surface of the label. Such imprinting may be conducted either before the label is applied to the capsule, or after. In the former instance, it is best to utilize conventional techniques such as offset printing, to apply the indicia to the labels, for example, before they are stamped out of a continuous film, or alternately, just prior to the application of adhesive thereto. In the instance where the labels are applied with a contactless technique as described just above, similar contactless printing may be utilized, by a device such as shown in FIG. 7 to avoid the unwanted fracture of the capsule. The application of indicia by imprinting provides a further visual characteristic that enhances the tamper-evident capabilities of the seal. As difficult as it is to cosmetically reconstruct a fractured seal, so much more so is the reconstruction of a fractured logo to assure alignment, continuity, etc. Imprinting, therefore, serves as a valuable additional step that enhances the tamper-evident qualities of the capsule seal prepared by the present invention.

Referring briefly to FIG. 5, capsule 10 is shown with a rounded label or patch 22 on which has been imprinted indicia 24. It can be seen that any dislocation of cap part 14 with respect to body part 16, would cause a disturbance of indicia 24 that would be extremely difficult to correct and virtually impossible to obscure.

A better understanding of the present invention can be gained from a review of the following illustrative examples, dealing with the preparation and application of various label materials. Unless otherwise specified all percentages of materials are expressed in percent by weight.

EXAMPLE I

An aqueous gelatin solution with a concentration of 30% by weight, comprising a 50/50 mixture of A 240 Bloom and B 150 Bloom gelatin materials was prepared, containing 2% of titanium dioxide and 0.25% yellow iron oxide, w/w on the basis of dry gelatin. This mixture was cast onto a lubricated flat glass plate through a slit of approximately 0.4 mm size, and at a temperature of 55° C. After the setting of gelatin, the film was dried on the glass plate in a climatic cabinet at 30° C. and 30% relative humidity until a water content of about 16% was attained. The films were then peeled off the plates and circular labels having diameters of 5 mm and thickness of about 0.04 mm were punched out for use as labels.

EXAMPLE II

A gelatin solution like that in Example I, however containing 0.2% red iron oxide, was cast onto a lubricated flat glass plate at a temperature of about 55° C. While wet and after 5 minutes of setting at room temperature, the films were dipped into an 8% aqueous glutaraldehyde solution, for 1 minute. The coated films were then dried under ambient room conditions overnight. The thickness of the dry films vary between 0.05 and 0.08 mm. Circular labels of 5 mm diameter were thereafter punched out.

EXAMPLE III

A 10% aqueous slurry of pregelatinized maize starch (type Presol D, Roquette National) was heated under stirring until a temperature of 90° C. was reached. The homogeneous dispersion appeared like a diluted sol, and was cast unto lubricated glass plates. The resulting films were dried under room conditions and were thereafter peeled off. The films had a thickness of about 0.05 to about 0.07 mm. Transparent labels of 5 mm diameter were punched out.

EXAMPLE IV

Labels were punched out of commercially available starch paper such as used in confectionery such as nougat. Three types of starch paper were tested, as follows:
1. Pure maize starch having a thickness of about 0.12 mm.
2. Maize starch, potatoe starch and vegetable grease.
3. Maize flour and pregelatinized maize starch. The film thicknesses of formulations 2 and 3 ranged from 0.10 to 0.3 mm.

EXAMPLE V

A 20% solution of hydroxypropylmethyl cellulose in water was obtained by stirring slowly at room temperature a mixture of 20 parts of Methocel E5 Premium (having a viscosity of 5 cps at 20° C. for a 2% aqueous solution) (Colorcon) and 80 parts of water. The resulting clear solution had a viscosity of about 2,000 to 2,500 cps at 20° C. This solution was cast unto lubricated glass plates at 30° C. through a slit of 0.5 mm. The films were dried overnight under room conditions and when peeled off had a thickness ranging from 0.04 to 0.065 mm. Rectangular labels were punched out with dimensions of 7 mm by 4 mm.

EXAMPLE VI 15 g of sorbitol, 0.9 grams of Ponceau 5X and 0.16 g of brilliant blue FCF are dissolved in 2.5 l of hot water, and the resulted solution is added to 520 g of a 15 cp type methyl cellulose. This mixture is stored at about 5° C. for 24 hours to allow the methyl cellulose to dissolve. At the end of this period, water is added in order to bring the volume to 2.7 l. The solution is well mixed and allowed to stand for de-bubbling. It is then cast onto lubricated glass plates. The resulting films are dried overnight at 20° C. and 40% relative humidity in a climatic cabinet. The dry films were peeled off and circular labels of a 6 mm diameter were punched out, having a film thickness of 0.6 mm.

EXAMPLE VII 50 ml of a 10% diethyl tartrate solution was prepared in water. 15 g of hydroxypropylmethyl cellulose phthalate (HP55F grade-Shin Etsu chemical) was added gradually under magnetic stirring. Thereafter, 100 ml of an aqueous 5% Citroflex solution was prepared after which alternative additions of 20 ml portions of Citroflex solution and 35 g portions of HP55 were added to the initial dispersion under magnetic stirring. Thereafter, the entire solution was de-bubbled under reduced vacuum.

37.5 ml of a 2% Methocel (K 15M grade, Colorcon) solution was prepared in water. To this solution, 0.5 g polypropylene glycol, 7.5 g of 5% Citroflex 2 solution and 5.62 g of pure Citroflex 2 were added in succession and under magnetic stirring. The homogeneity of theresulting emulsion was controlled.

The above emulsion was added to the dispersion of HP55 under constant stirring. The ratio between the dispersion and the emulsion of Methocel was kept as closely as possible to 3.9. The resulting dispersion was stored at room temperature overnight. Thereafter films were cast on lubricated glass plates at room temperature, and were thereafter dried for 1 hour at 60° C., whereupon they were peeled off. Labels having diameters of 4 and 6 mm respectively, were punched out of the sheets, and were found to be clear and transparent. The label bore a thickness ranging from 0.045 to 0.062 mm.

EXAMPLE VIII 10 g of hydroxypropylmethyl cellulose phthlate (HP55F grade) were vigorously mixed with 24 g of ethyl acetate, 6 g of 2-butanol, 11 g of 2-butoxyethanol and 2 of Tween 80. After total dissolution of the HP55F, a dispersion of 0.2 g titanium dioxide (Arathase grade) in 10 g of water was gradually added. A homogeneous emulsion was obtained and with the film casting procedures described earlier herein, white opaque films having thicknesses of about 0.05 mm were obtained, after drying overnight at 50° C. Circular labels having a 5 mm diameter were thereafter punched out.

EXAMPLE IX 7 g of cellulose acetate phthalate are mixed with 2.4 g triacetin, 23.5 g ethyl acetate, 8 g of 2-butanol and 8 g of butyl glycol. After the dissolution of the cellulose acetate phthalate at the refluxing temperature of ethylacetate (77° C.), a dispersion of 0.2 g titanium dioxide and 0.2 g red iron oxide in 10 ml of ethylacetate was added and homogeneously mixed therewith. Utilitizing the standard film casting procedure described above, pink opaque films having a thickness of 0.04 mm were obtained. The films were dried overnight at 50° C. and thereafter circular labels having a 5 mmdiameter were punched out.

EXAMPLE X

A mixture of 25 g of a copolymer of methylacrylic acid and methylacrylic acid methyl ester (Eudragit L100) and 2.5 g polyethylene glycol 4000, 29 g of acetone and 43.5 g of isopropanol were heated together under reflux until complete dissolution of the methylacrylic copolymer was achieved. The hot mixture was then sprayed onto a teflon sheet, and after 3 hours of drying at 50° C., a transparent film having a thickness of about 0.05 mm was obtained. Thereafter, circular labels of a 5 mm diameter were punched out.

EXAMPLE XI

Hard shelled gelatin capsules size No. 1, filled with lactose are sealed with individual circular gelatin labels prepared in accordance with Example I, above. Individual labels were picked up by a labeling roll exerting a vacuum suction. Each label was sequentially indexed past a nozzle having a 0.3 mm orifice through which a quantity of steam was applied against the labels to render them sticky. The labels were then indexed into position adjacent the capsules, the vacuum in the label roller was broken and application rolls adjacent the vacuum roll assured the uniform adhesion of the labels to the capsule surface by rotating the capsule therepast. The labeled capsules were dried in an air flow, and dried capsules having approximately 16% water in the shell, could not be opened without distroying the label and the capsule.

EXAMPLE XII

The same capsule, contents and label material were combined herein. In this example, however, the steam spray system was replaced by a roller coating that transferred 10 microliters of water at a temperature 95° C. to each label by means of hydrophilic felt rolls. The capsules prepared in accordance with this embodiment exhibited the same resistance to tampering.

EXAMPLE XIII

This Example is similar to Example XII with the exception that the film forming material comprised starch paper prepared in accordance with Example IV above. Also, a spray of 5 to 10 microliters of hot water replaced the steam spray of Example XI and two labels were applied over the seam of each capsule. The resulting capsules exhibited the same resistance to tampering as with Examples XI and XII, above.

EXAMPLE XIV

A white opaque film as described in Example VIII was imprinted with a logo by conventional offset printing with a black ink containing shellac EPC Grade and black iron oxide. Round labels of 5 mm diameter were punched out and put into a label magazine of a conventional labelling machine adapted for small cylindrical objects.

A hot phosphate buffer solution having a pH of 6.8 and a temperature of 60° C. was applied to the unprinted side of the labels by a roller coating procedure performed while the labels were maintained in fixed position upon a vacuum roll. The labels were then affixed to the capsule and additional drying thereof was conducted. The resulting capsules could not be opened without destroying the label and the capsule.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

I claim:

1. A method for sealing edible non-enteric capsules comprising telescopically engaged tubular capsule halves defining a junction seam and containing pharmaceutical ingredients, for the purpose of rendering such capsules tamper-proof and temper-evident, said method comprising adhesively bonding against at least a portion of said seam, a frangible edible label adapted to cover said seam at the point of intersection therewith and to fracture upon displacement of said capsule halves with respect to each other.

2. The method of claim 1 wherein said label is prepared as a film, and said film is adhesively bonded to said seam.

3. The method of claim 2 wherein said film is prepared by casting an edible film forming material against a flat molding surface.

4. The method of claim 3 wherein said film is dried and thereafter cut to form said label.

5. The method of claim 3 wherein said film forming material is selected from the group consisting of natural proteins, cellulose, cellulose derivatives, carbohydrates, vinyl polymers, acrylic polymers, natural gums and mixtures thereof.

6. The method of claim 5 wherein said film forming material is selected from the group consisting of gelatin, collagen, cellulose, cellulose derivatives, starches, modified starches, polyvinyl acetate, polymethacrylic acid, polyacrylic acid, polymethyl methacrylate, gum arabic, gum tragacanth, locust bean gum, guar gum, and mixtures thereof.

7. The method of claim 3 wherein said film forming material is prepared in solution, with an edible solvent selected from the group consisting of water, lower alkanols, glycols, glycol ethers, lower alkyl ketones, lower alkyl carboxylic acids, and mixtures thereof.

8. The method of claim 7 wherein said film forming material is selected from the group consisting of gelatin, collagen, cellulose, cellulose derivatives, starches, modified starches, polyvinyl acetate, polymethacrylic acid, polyacrylic acid, polymethyl methacrylate, gum arabic, gum tragacanth, locust bean gum, guar gum, and mixtures thereof.

9. The method of claim 3 wherein said film forming material further includes a material selected from the group consisting of softeners, colorants, lubricants, antioxidants, and mixtures thereof.

10. The method of claim 9 wherein said film forming material is selected from the group consisting of gelatin, collagen, cellulose, cellulose derivatives, starches, modified starches, polyvinyl acetate, polymethacrylic acid, polyacrylic acid, polymethyl methacrylate, gum arabic, gum tragacanth, locust bean gum, guar gum, and mixtures thereof.

11. The method of claim 2 wherein said film is first coated on one side thereof with an edible adhesive compatable with said label and the material constituting said capsule, and is thereafter applied to said seam with said edible adhesive positioned therebetween.

12. The method of claim 11 wherein said edible adhesive is applied in the heated condition.

13. The method of claim 12 wherein said adhesive is applied by spraying.

14. The method of claim 13 wherein said adhesive comprises a hot melt.

15. The method of claim 13 wherein said adhesive is in the vaporized state.

16. The method of claim 11 wherein said adhesive is selected from the group consisting of water and steam.

17. The method of claim 11 wherein said adhesive comprises an aqueous solution of a material selected from the group consisting of acidic buffer solutions, lower alkanols, natural proteins, carbohydrates, cellulose derivatives, gums, vinyl polymers, and mixtures thereof.

18. The method of claim 11 wherein said adhesive is selected from the group consisting of cross-linking synthetic monomers, natural and synthetic resins in low boiling point organic solvent solutions, polymer melts, and mixtures thereof.

19. The method of claim 11 wherein said adhesive is pressure-sensitive.

20. The method of claim 19 wherein said adhesive is selected from the group consisting of wood rosin derivatives, terpene derivatives, coumarone-indene resins, natural rubbers, synthetic rubbers, acrylic polymers and copolymers, and mixtures thereof.

21. The method of claim 1 wherein said label comprises a longitudinal strip disposed annularly about said seam.

22. The method of claim 1 wherein said label comprises a longitudinal strip extending annularly about the entirety of said seam, and said label cooperates with said capsule walls to render said capsule fluid-tight.

23. The method of claim 1 wherein said said label comprises a longitudinal strip disposed transversely across said seam.

24. The method of claim 1 wherein said label comprises a round patch disposed across said seam along a portion thereof.

25. The method of claim 1 including printing visible indicia on the surface of said label visible when said label is affixed to said capsule.

26. The method of claim 25 wherein said printing is performed on said label prior to applying said label to said capsule.

27. The method of claim 25 wherein said printing is performed on said label subsequent to the application of said label to said capsule.

28. The method of claim 1 wherein said label is prepared as a hot melt liquid and is applied against said seam while in the heated liquid state.

29. The method of claim 28 wherein said label is applied by a jet printing technique.

30. The method of claim 1 wherein said label is self-adhesive.

* * * * *